US00PP23273P2

(12) United States Plant Patent
Pieters

(10) Patent No.: US PP23,273 P2
(45) Date of Patent: Dec. 25, 2012

(54) ***CHRYSANTHEMUM* PLANT NAMED 'BRONZE PAMPLONA JOGGER'**

(50) Latin Name: *Chrysanthemum×morifolium*
Varietal Denomination: Bronze Pamplona Jogger

(75) Inventor: Luc Remi Johan Pieters, Staden-Oostnieuwkerke (BE)

(73) Assignee: Pieters Joseph + Luc B.V.B.A., Staden-Oostnieuwkerke (BE)

( * ) Notice: Subject to any disclaimer, the term of this patent is extended or adjusted under 35 U.S.C. 154(b) by 48 days.

(21) Appl. No.: 13/066,464

(22) Filed: Apr. 14, 2011

(51) Int. Cl.
*A01H 5/00* (2006.01)

(52) U.S. Cl. ..... Plt./290

(58) Field of Classification Search ..... Plt./290
See application file for complete search history.

(56) References Cited

OTHER PUBLICATIONS

UPOV-PLUTO Plant Variety Database, 2011-06, cultivar 'Bronze Pamplona Jogger'.*

* cited by examiner

*Primary Examiner* — Susan McCormick Ewoldt
(74) *Attorney, Agent, or Firm* — C. A. Whealy

(57) ABSTRACT

A new and distinct cultivar of *Chrysanthemum* plant named 'Bronze Pamplona Jogger', characterized by its uniform, upright, outwardly spreading and rounded plant habit; moderately vigorous growth habit; freely branching habit; dense and full plant habit; freely flowering habit; large decorative-type inflorescences with greyed orange-colored ray florets; long flowering period; and excellent garden performance.

2 Drawing Sheets

Botanical designation: *Chrysanthemum×morifolium.*
Cultivar denomination: 'BRONZE PAMPLONA JOGGER'.

CROSS-REFERENCED TO CLOSELY-RELATED APPLICATIONS

Title: *Chrysanthemum* Plant Named 'Dark Pamplona Jogger'
Applicant: Luc Remi Pieters
Filed: Concurrently with this application application Ser. No. 13/066,462
Title: *Chrysanthemum* Plant Named 'White Pamplona Jogger'
Applicant: Luc Remi Pieters
Filed: Concurrently with this application, now U.S. Plant Pat. No. 22,596
Title: *Chrysanthemum* Plant Named 'Yellow Pamplona Jogger'
Applicant: Luc Remi Pieters
Filed: Concurrently with this application, now U.S. Plant Pat. No. 22,409

BACKGROUND OF THE INVENTION

The present invention relates to a new and distinct cultivar of *Chrysanthemum* plant, botanically known as *Chrysanthemum×morifolium* and hereinafter referred to by the name 'Bronze Pamplona Jogger'.

The new *Chrysanthemum* plant is a naturally-occurring whole plant mutation of *Chrysanthemum×morifolium* 'Pamplona Jogger', not patented. The new *Chrysanthemum* plant was discovered and selected by the Inventor as a flowering plant from within a population of plants of 'Pamplona Jogger' in a controlled greenhouse environment in Staden-Oostnieuwkerke, Belgium in October, 2007.

Asexual reproduction of the new *Chrysanthemum* plant by vegetative cuttings was first conducted in a controlled greenhouse environment in Staden-Oostnieuwkerke, Belgium in January, 2008. Asexual reproduction by cuttings has shown that the unique features of this new *Chrysanthemum* plant are stable and reproduced true to type in successive generations.

SUMMARY OF THE INVENTION

Plants of the new *Chrysanthemum* have not been observed under all possible environmental conditions and cultural conditions. The phenotype may vary somewhat with variations in environment such as temperature, daylength and light intensity, without, however, any variance in genotype.

The following traits have been repeatedly observed and are determined to be the unique characteristics of 'Bronze Pamplona Jogger'. These characteristics in combination distinguish 'Bronze Pamplona Jogger' as a new and distinct *Chrysanthemum* plant:

1. Uniform, upright, outwardly spreading and rounded plant habit; moderately vigorous growth habit.
2. Freely branching habit; dense and full plant habit.
3. Freely flowering habit.
4. Large decorative-type inflorescences with greyed orange-colored ray florets.
5. Long flowering period.
6. Excellent garden performance.

Plants of the new *Chrysanthemum* differ primarily from the parent, 'Pamplona Jogger', in ray floret color as plants of 'Pamplona Jogger' have pink-colored ray florets.

Plants of the new *Chrysanthemum* can be compared to plants of *Chrysanthemum×morifolium* 'Tardel', not patented. In side-by-side comparisons conducted in Staden-Oostnieuwkerke, Belgium, plants of the new *Chrysanthemum* differed from plants of 'Tardel' in the following characteristics:

1. Plants of the new *Chrysanthemum* had larger inflorescences than plants of 'Tardel'.
2. Plants of the new *Chrysanthemum* had decorative type inflorescences whereas plants of 'Tardel' had daisy type inflorescences.
3. Ray florets of the new *Chrysanthemum* were greyed orange in color whereas ray florets of plants of 'Tardel' were yellow in color.

Plants of the new *Chrysanthemum* can also be compared to plants of *Chrysanthemum×morifolium* 'Dark Pamplona Jogger', disclosed in a U.S. Plant Patent application filed concurrently, *Chrysanthemum×morifolium* 'White Pamplona Jogger', disclosed in a U.S. Plant Patent application filed concurrently, and *Chrysanthemum×morifolium* 'Yellow Pamplona Jogger', disclosed in a U.S. Plant Patent application filed concurrently. In side-by-side comparisons conducted in Staden-Oostnieuwkerke, Belgium, plants of the new *Chrysanthemum* differ primarily from plants of 'Dark Pamplona Jogger', 'White Pamplona Jogger' and 'Yellow Pamplona Jogger' in ray floret color.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering plant of 'Bronze Pamplona Jogger' grown in a container.

The photograph on the second sheet are close-up views of the upper and lower surfaces of typical inflorescences (left) of 'Bronze Pamplona Jogger' and upper and lower surfaces of typical leaves (right) of 'Bronze Pamplona Jogger'.

DETAILED BOTANICAL DESCRIPTION

The aforementioned photographs and following observations and measurements describe plants grown during the summer and autumn in 19-cm containers in an outdoor nursery in Staden-Oostnieuwkerke, Belgium and under conditions and practices which approximate those generally used in commercial *Chrysanthemum* production. During the production of the plants, day temperatures ranged from 10° C. to 25° C. and night temperatures ranged from 5° C. to 15° C. Plants were 5.5 months old when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Bronze Pamplona Jogger'.

Parentage: Naturally-occurring whole plant mutation of *Chrysanthemum×morifolium* 'Pamplona Jogger', not patented.

Propagation:

*Type*.—Terminal vegetative cuttings.

*Time to initiate roots, summer*.—About 14 days at temperatures of about 20° C.

*Time to initiate roots, winter*.—About 20 days at temperatures of about 20° C.

*Time to produce a rooted young plant, summer*.—About 30 days at temperatures of about 20° C.

*Time to produce a rooted young plant, winter*.—About 40 days at temperatures of about 20° C.

*Root description*.—Fine, fibrous; light brown in color.

*Rooting habit*.—Freely branching; medium density.

Plant description:

*Appearance*.—Perennial *Chrysanthemum* with decorative type inflorescences; stems upright and outwardly spreading giving a uniformly rounded appearance to the plant; very freely branching habit with about 25 lateral branches developing per plant; pinching enhances lateral branch development; dense and full plant habit; moderately vigorous growth habit.

*Plant height*.—About 37 cm.

*Plant width*.—About 65 cm.

*Lateral branches*.—Length: About 25.5 cm. Diameter: About 4 mm. Internode length: About 2 cm. Strength: Strong. Aspect: Lateral branches positioned about 30° from the main stem. Texture: Densely pubescent; longitudinally ridged. Color: Close to 146B.

*Leaves*.—Arrangement: Alternate, simple. Length: About 3.8 cm. Width: About 2.4 cm. Shape: Roughly ovate, three-lobed. Apex: Acute. Base: Attenuate. Margin: Palmately lobed and coarsely dentate, sinuses between lateral lobes divergent to parallel. Texture, upper and lower surfaces: Densely pubescent. Venation pattern: Pinnate. Color: Developing leaves, upper surface: Close to N137B. Developing leaves, lower surface: Close to 137B. Fully expanded leaves, upper surface: Close to N137B; venation, close to 147B. Fully expanded leaves, lower surface: Close to 147B; venation, close to 147B. Petiole: Length: About 1 cm. Diameter: About 1.5 mm. Texture, upper and lower surfaces: Densely pubescent. Color, upper surface: Close to 137A. Color, lower surface: Close to 138A.

Inflorescence description:

*Appearance*.—Decorative inflorescence form; inflorescences borne on terminals above foliar plane; disc and ray florets arranged acropetally on a capitulum.

*Fragrance*.—Moderately fragrant, pungent.

*Flowering response*.—Long flowering period; under natural season conditions, plants flower continuously from mid-September to late October in Belgium.

*Postproduction longevity*.—Inflorescences maintain good color and substance for about three weeks in an outdoor nursery; inflorescences not persistent.

*Quantity of inflorescences*.—About 45 inflorescences develop per lateral branch; about 1,250 inflorescences per plant.

*Inflorescence bud*.—Height: About 8 mm. Diameter: About 8 mm. Shape: Broadly ovate. Color: Close to 147B.

*Inflorescence size*.—Diameter: About 4.7 cm. Depth (height): About 1.7 cm. Disc diameter: About 9 mm. Receptacle diameter: About 3 mm. Receptacle height: About 3 mm. Receptacle color: Close to 144D.

*Ray florets*.—Length: About 2.3 cm. Width: About 5 mm. Shape: Narrowly obovate to oblanceolate. Apex: Obtuse to broadly acute. Base: Cuneate. Margin: Entire. Aspect: About 70° from vertical. Texture, upper and lower surfaces: Smooth, glabrous; longitudinally ridged. Number of ray florets per inflorescence: About 80. Color: When opening, upper surface: Close to 165C and 167C to 167D; at the base, close to 144C. When opening, lower surface: Close to 174B to 174C; at the base, close to 144C. Fully opened, upper surface: Close to 164C; at the base, close to 150C to 150D; color becoming closer to 162A to 162B with development. Fully opened, lower surface: Close to N170D; at the base, close to 144C to 144D; color does not change with development.

*Disc florets*.—Length: About 1.2 cm. Diameter: About 1 mm. Shape: Tubular, filiform; apices narrowly acute. Texture, inner and outer surfaces: Smooth, glabrous. Number of disc florets per inflorescence: About 50 massed at the center of the inflorescence. Color, immature: Close to 174B to 174C; at the apex, close to 164B; at the base, close to 150C. Color, mature: Close to 164C and 165C; at the base, close to 150C.

*Phyllaries*.—Number of phyllaries per inflorescence: About 24 arranged in about three whorls. Length: About 5 mm. Width: About 2.5 mm. Shape: Ovate. Apex: Bluntly acute. Base: Cuneate. Margin: Entire. Texture, upper surface: Smooth, glabrous. Texture, lower surface: Pubescent. Color, upper surface: Close to 147C; margins, close to 199A. Color, lower surface: Close to 147B; margins, close to 199A.

*Peduncles*.—Length, terminal peduncle: About 5.9 cm. Length, fourth peduncle: About 5.1 cm. Diameter: About 1.7 mm. Aspect: Erect to about 25° from vertical. Strength: Strong. Texture: Densely pubescent. Color: Close to 138B.

*Reproductive organs*.—Androecium: Not observed. Gynoecium: Present only on ray florets. Quantity: One pistil per floret. Pistil length: About 3 mm. Style length: About 2 mm. Style color: Close to N144B. Stigma shape: Cleft, decurrent. Stigma color: Close to N144B. Ovary color: Close to 144C to 144D.

*Seed/fruit*.—Seed and fruit production have not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance, are hardy to USDA Hardiness Zones 7 to 8 and will tolerate high temperatures of about 35° C.

It is claimed:

1. A new and distinct *Chrysanthemum* plant named 'Bronze Pamplona Jogger' as illustrated and described.

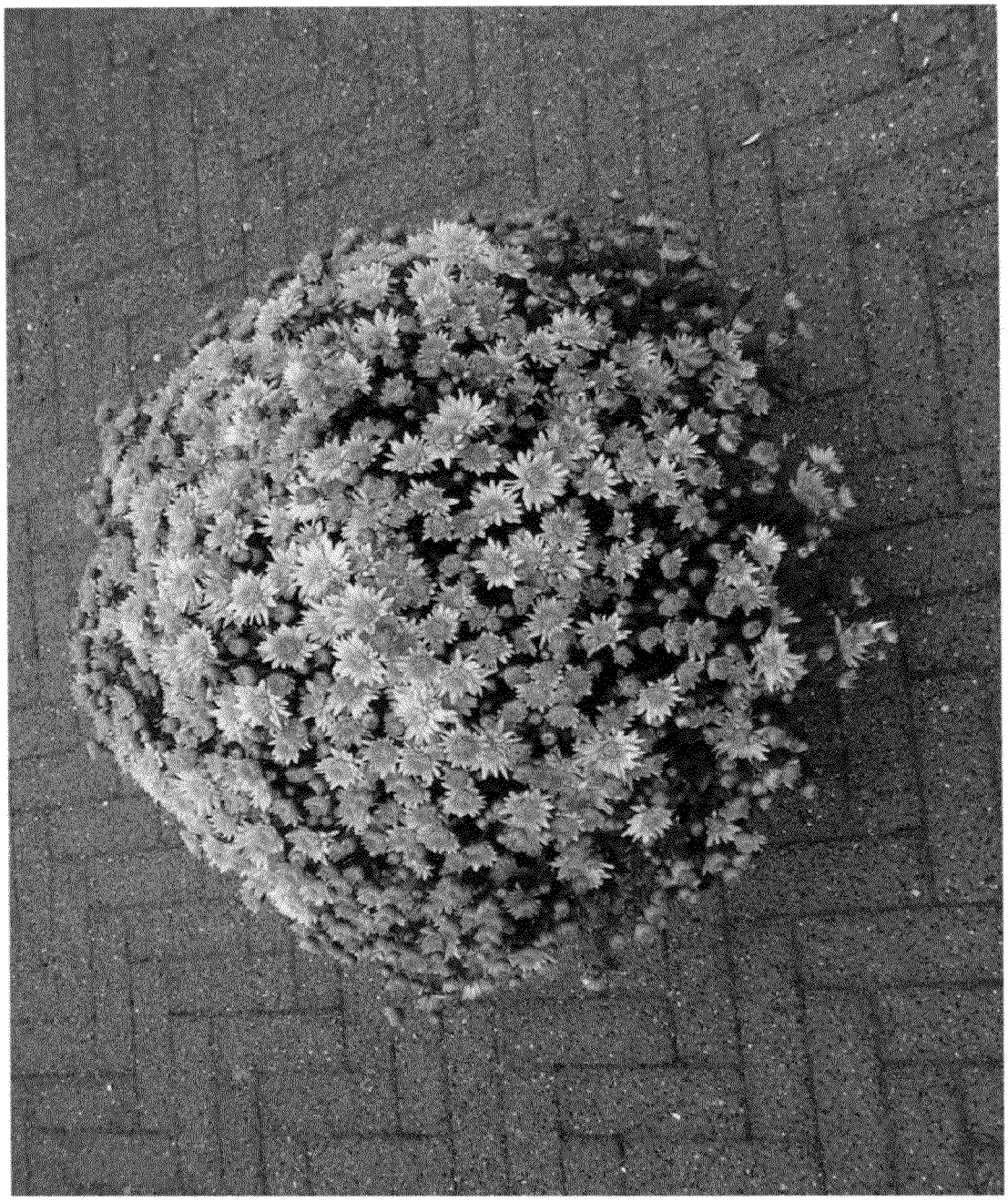

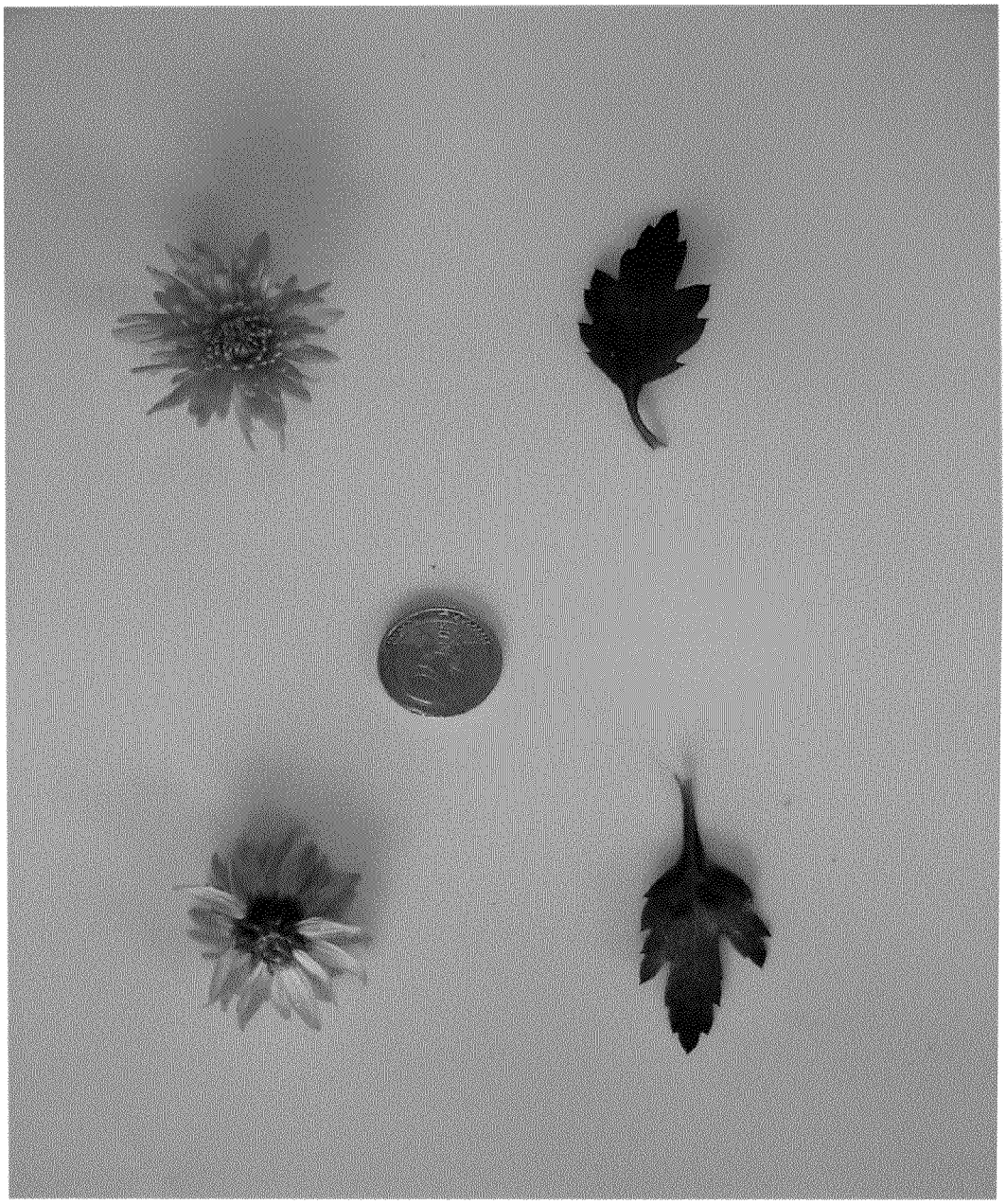

* * * * *